(12) United States Patent
Braiman et al.

(10) Patent No.: US 7,517,968 B2
(45) Date of Patent: Apr. 14, 2009

US007517968B2

(54) RAPID AND INEXPENSIVE METHOD FOR THE PURIFICATION OF PROTEORHODOPSIN

(75) Inventors: Mark S. Braiman, Cazenovia, NY (US); Ranga Partha, Houston, TX (US)

(73) Assignee: Syracuse University, Syracuse, NY (US)

( * ) Notice: Subject to any disclaimer, the term of this patent is extended or adjusted under 35 U.S.C. 154(b) by 464 days.

(21) Appl. No.: 10/886,782

(22) Filed: Jul. 7, 2004

(65) Prior Publication Data

US 2005/0148762 A1 Jul. 7, 2005

Related U.S. Application Data

(60) Provisional application No. 60/485,272, filed on Jul. 7, 2003.

(51) Int. Cl.
*C07K 14/00* (2006.01)
*A23J 1/00* (2006.01)

(52) U.S. Cl. ........................ 530/418; 530/355; 530/412; 530/350

(58) Field of Classification Search ........................ None
See application file for complete search history.

(56) References Cited

U.S. PATENT DOCUMENTS

| | | | | |
|---|---|---|---|---|
| 5,776,770 | A * | 7/1998 | Schnitzer | 435/317.1 |
| 5,877,298 | A * | 3/1999 | Fahim et al. | 530/412 |
| 6,121,427 | A * | 9/2000 | Yang et al. | 530/412 |
| 6,383,778 | B1 * | 5/2002 | Zuker et al. | 435/69.1 |

OTHER PUBLICATIONS

Sarramegna et al., Recombinant G protein-coupled receptors from expression to renaturation: a challenge towards structure, 2006, Cellular Molecular Life Science, vol. 63, pp. 1149-1164.*
Lundstrom et al., Structural biology of G protein-coupled receptors, 2005, Bioorganic and Medicinal Chemistry Letters, vol. 15, pp. 3654-3657.*
Kelemen et al., Proteorhodopsin in living color: diversity of spectral properties within living bacterial cells, 2003, Biochemica et Biophysica Acta, vol. 1618, pp. 25-32.*
Devesa et al., Functional reconstitution of the HIV receptors CCR5 and CD4 in liposomes, 2002, European Journal of Biochemistry, vol. 269, pp. 5163-5174.*
Harris et al. Protein Purification Methods: a practical approach, Oxford University Press, 1989.*
Béjà et al., "Bacterial Rhodopsin: Evidence for a New Type of Phototrophy in the Sea," *Science*, 289:1902-1906 (2000).
Béjà et al., "Proteorhodopsin Phototrophy in the Ocean," *Nature*, 411:786-789 (2001).
Birge, R.R., "Photophysics and Molecular Electronic Applications of the Rhodopsins," *Annu. Rev. Phys. Chem.*, 41:683-733 (1990).

Brown et al., "Estimated Acid Dissociation Constants of the Schiff Base, Asp-85, and Arg-82 During the Bacteriorhodopsin Photocycle," *Biophys. J.*, 65:124-130 (1993).
Bunkin et al., "Diffraction Efficiency of Bacteriorhodopsin and its Analogs," *Sov. Tech. Phys. Lett.*, 7(12):630-631 (1981).
Dioumaev et al., "Proton Transfers in the Photochemical Reaction Cycle of Proteorhodopsin," *Biochemistry*, 41:5348-5358 (2002).
Drachev et al., "Reconstitution of Biological Molecular Generators of Electric Current," *J. Biol. Chem.*, 251(22):7059-7065 (1976).
Friedrich et al., "Proteorhodopsin is a Light-Driven Proton Pump with Variable Vectoriality," *J. Mol. Biol.*, 321:821-838 (2002).
Hampp et al., "Bacteriorhodopsin and its Functional Variants as New Materials for Optical Information Processing," *European Conference of Biotechnology (EIT)*, 124-128 (1988).
Hampp et al., "Optical Properties of Polymeric Films of Bacteriorhodopsin and its Functional Variants: New Materials for Optical Information Processing," *SPIE*, 1125:2-8 (1989).
Hampp et al., "Bacteriorhodopsin Wildtype and Variant Aspartate-96 → Asparagine as Reversible Holographic Media," *Biophys. J.*, 58:83-93 (1990).
Hampp et al., "Bacteriorhodopsin as a Reversible Holographic Medium in Optical Processing," *IEEE EMBS*, 12(4):1719-1720 (1990).
Hampp et al., "Fringemaker—the First Technical System Based on Bacteriorhodopsin," *Bioelectronic Applications of Photochromic Pigments*, IOS Press, Szeged, Hungary, pp. 44-53 (2000).
Krebs et al., "Detection of Fast Light-Activated H+ Release and M Intermediate Formation from Proteorhodopsin," *BMC Physiol.*, 2:1-8 (2002).
Oesterhelt, D., "Photosynthetic Systems in Prokaryotes: The Retinal Proteins of Halobacteria and the Reaction Centre of Purple Bacteria," *Biochemistry Intern.*, 18(4):673-694 (1989).
Spudich, J.L., "A Chloride Pump at Atomic Resolution," *Science*, 288:1358-1359 (2000).
Stuart et al., "Biomolecular Electronic Device Applications of Bacteriorhodopsin," in *Molecular Electronics: Biosensors and Biocomputers*, L. Barsanti et al. (eds.), Kluwer Academic Publishers, pp. 265-299 (2003).
Haga et al., "G-Protein Coupled Receptors," CRC Press (Preface), (1999).
Palczewski et al., "Crystal Structure of Rhodopsin: A G Protein-Coupled Receptor," *Science*, 289:739-745 (2000).

* cited by examiner

*Primary Examiner*—Robert Landsman
*Assistant Examiner*—Ian Dang
(74) *Attorney, Agent, or Firm*—Nixon Peabody LLP

(57) ABSTRACT

A method for purifying a membrane protein is disclosed which includes providing a test sample potentially including a target membrane protein; adding incremental amounts of a precipitating agent to the test sample to form one or more mixtures; and treating the one or more mixtures under conditions effective to obtain precipitated, purified target membrane protein if present in the test sample.

21 Claims, 5 Drawing Sheets

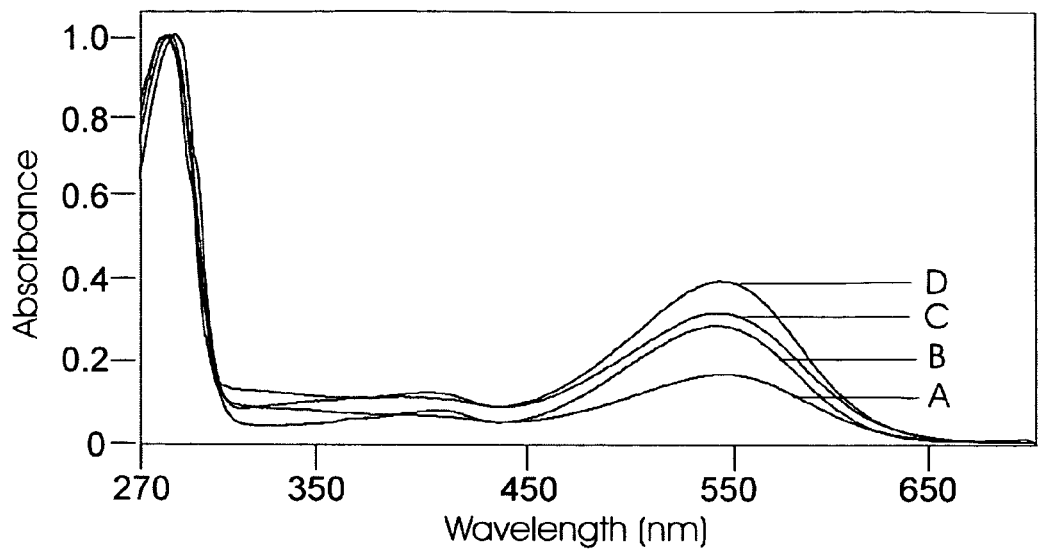

UV/visible absorption spectra of pR at various stages of purification. All four spectra were measured in the presence of 3% octylglucoside at pH 7.1. Each sample was diluted to 1 OD at the 280-nm protein peak. Spectrum A, the octylglucoside extract of *E. coli* membranes; spectrum B, pR precipitated once using citrate solution; spectrum C, pR precipitated twice using sodium citrate; spectrum D, same material after purifying through a Ni-Resin column.

FIGURE 1

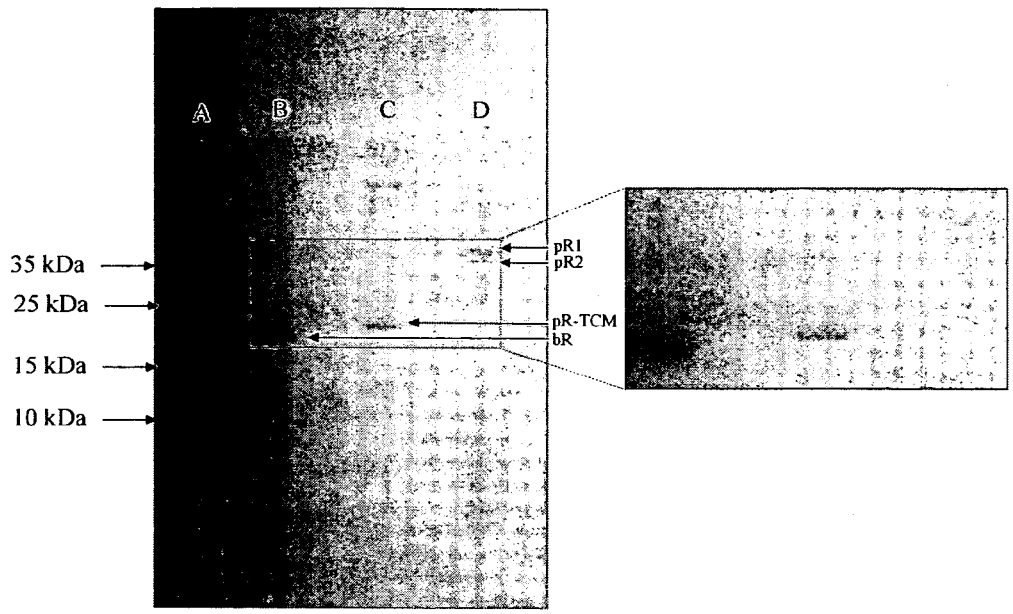

SDS-PAGE of pR (wild type and pR-triple cysteine mutant). Lane A contains ProSieve® protein molecular weight markers with labeled bands at 10, 15, 25 and 35 kDa. Lane B contains bR. Lane C is of the pR triple cysteine mutant (TCM) and Lane D contains pR wild type(+$His_6$) protein, both purified by using the citrate method followed by a Ni-NTA column. All samples were treated with β-mercaptoethanol (2.5% v/v) prior to loading. Inset shows a magnified portion of the gel.

FIGURE 2

Schematic representation of the citrate purification procedure with the timeline.

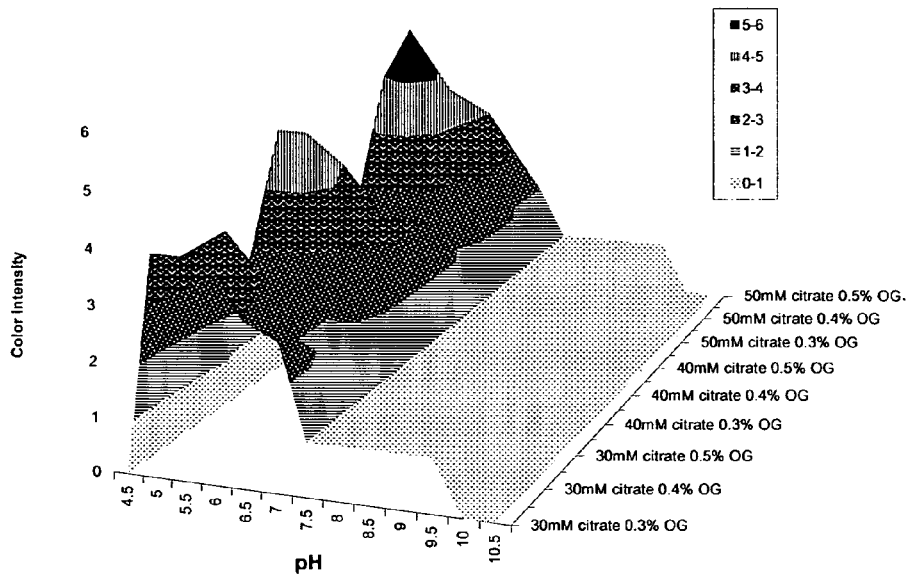

Three-dimensional plot representing the best possible condition for the precipitation of pR. Color intensity is numbered from 0 to 6, where 0 represents no precipitation and 6 represents the most-colored precipitate. The most intense colored pR precipitate was obtained at pH 5.5 using 50 mM sodium citrate as a precipitant, with the concentration of octylglucoside reduced to 0.3%.

FIGURE 4

Pellets of pR mutants (D97N, R94CD97N, R94C, E108D) obtained from precipitation using Sodium citrate. The first tube contains wild-type pR in the supernatant before precipitation. The grey pellet represents impure protein. These results demonstrate the applicability of this purification method to mutants of pR.

RAPID AND INEXPENSIVE METHOD FOR THE PURIFICATION OF PROTEORHODOPSIN

This application claims the benefit of U.S. Provisional Patent Application Ser. No. 60/485,272, filed Jul. 7, 2003, which is herein incorporated by reference in its entirety.

FIELD OF THE INVENTION

The present invention relates to the purification of proteorhodopsin, particularly to a method for the rapid and inexpensive purification of proteorhodopsin.

BACKGROUND OF THE INVENTION

Proteorhodopsin (pR) is a bacterial light-driven proton pump with several physico-chemical properties similar to those of its archaeal homolog bacteriorhodospin (bR). Currently, there is at least 1 commercial device utilizing bR, a holographic interferometer (the Fringemaker®). The related protein pR is a recently discovered retinal protein with some properties strikingly similar to those of bR, while other properties are different and better suited for certain potential applications. An ability to produce and purify protein inexpensively in large quantities is an important pre-requisite for commercializing pR as a biomaterial. Methods for expressing pR heterologously in *E. coli* in a functional form have been described previously, but these methods produce pR at a level of <0.1% of total cell dry weight, and require expensive and/or time-consuming column chromatographies to produce pR at a concentration suitable for use in devices.

Technology using biological materials as platforms for developing various electronic and computational devices at the molecular level has advanced greatly in the last decade. The search for biological molecules that can function as durable photochromic materials for information storage and processing is accelerating. Bacteriorhodospin (bR), a light-driven proton pump, mediating photosynthesis in Halobacteria (Oesterhelt, 1989), has long stood out as an important contender for various technical applications in the field of molecular electronics. The ease of preparation of bR in large quantities, coupled with its thermal and photochemical stability, were key factors for investigating its use in holography (Bunkin et al, 1981; Hampp et al, 1988, 1989), optical information processing (Hampp et al, 1990), and other human-invented applications, as well as its natural function of solar energy conversion (Drachev et al, 1976). Genetic engineering has further aided by producing variants of bR with more attractive features (Birge at al, 1990). (For a review of further device applications, see Stuart et al, 2003).

Although the research involving bR as a material for information processing has multiplied enormously, there has been only one commercial product developed where bR is used as a functional component, the Fringemaker® holographic interferometer (Hampp and Juchem, 2000). This calls for exploring newer biological materials with similar properties as bR that might have potential utility in the field of molecular electronics.

Proteorhodopsin (pR), the first-discovered eubacterial homolog of bR, was recently identified from the DNA sequences of several uncultured species of γ-proteobacteria, which are a component of marine planktons present in the ocean surface waters (Béjà et al., 2000, 2001). It is a 249-amino-acid polypeptide with 7 transmembrane α-helices having a retinal co-factor attached to $Lys^{231}$ to form a protonated Schiff base. When expressed heterologously in *E. coli*, the pR contained in the bacterial membranes was shown to act as a light-driven proton pump, producing a proton motive force that could be (presumably) be further converted into chemical energy (Béjà et al, 2000). The discovery of a bR homolog in the bacterial kingdom is scientifically significant, since all three kingdoms of life are now known to possess genes for proteins in the bR superfamily. pR is believed to play an important role in the energy balance of the earth due to presence of extensive biomass of marine bacterioplanktons.

In pR, $Asp^{97}$ and $Glu^{108}$ almost certainly function respectively as the proton acceptor from, and donor to, the Schiff base (Béjà et al, 2000; Krebs et al, 2002; Dioumaev et al, 2002; Friedrich et al, 2002). These residues are homologous to $Asp^{85}$ and $Asp^{96}$ in bR. At pH 9.5 the photocycle of pR was proposed to have pR, pK, pM, pN and pO photointermediate states, quite similar to the bR photocycle, which has six principal photointermediate states: bR, K, L, M, N and O. There is also evidence of a fast (<100 µs) light-triggered proton release from pR at pH>9.0 (Krebs et al. 2002), as also observed in bR. These are just a few of the similarities between pR and bR.

However, one can also find sharp differences between a number of physiochemical attributes of these two proteins. For example, the $pK_a$ of the proton acceptor $Asp^{97}$ in pR in the unphotolyzed state is at least 7.0 (Dioumaev et al. 2002; Friedrich et al. 2002), and in fact for pure protein is closer to 8.2 (Partha et al. 2004). This is 5.5 units more than the $pK_a$ (2.5) of the homologous residue in bR, $Asp^{85}$ (Brown et al. 1993). The spectral maximum of pR is also significantly blue shifted; pR absorbs maximally at 545 nm at pH 7.0 and at 520 nm at pH 9.0, whereas bR absorbs maximally at 570 nm at both these pH values.

Proteorhodopsin has been previously purified using adsorption/affinity chromatography using Phenylsepharose™, hydroxyapatite and/or Ni-NTA resin (Dioumeav et al. 2002; Krebs et al. 2002). To allow purification by using Ni-NTA resin, pR had been cloned into the pBAD-TOPO vector with a 6×His-tag at the C-terminus (Béjà et al. 2000).

SUMMARY OF THE INVENTION

In accordance with one aspect of the present invention, there is provided a method for purifying a membrane protein including: providing a test sample potentially including a target membrane protein; adding incremental amounts of a precipitating agent to the test sample to form one or more mixtures; and treating the one or more mixtures under conditions effective to obtain precipitated, purified target membrane protein if present in the test sample.

In accordance with another aspect of the present invention, there is provided a method for purifying proteorhodopsin including: providing a test sample potentially including proteorhodopsin; adding incremental amounts of citric acid or a salt thereof to the test sample to form one or more mixtures; and treating the one or more mixtures under conditions effective to obtain precipitated, purified proteorhodopsin if present in the test sample.

These and other aspects of the present invention will become apparent upon a review of the following detailed description and the claims appended thereto.

BRIEF DESCRIPTION OF THE DRAWINGS

FIG. 1 is a UV/visible absorption spectra of pR at various stages of purification.

FIG. 2 is a sodium dodecylsufate polyacrylamide gel electrophoresis of pR.

FIG. 4 is a three-dimensional plot of color intensity of the precipitate verses pH for the precipitation of pR.

DETAILED DESCRIPTION OF PREFERRED EMBODIMENTS

Figure 3:
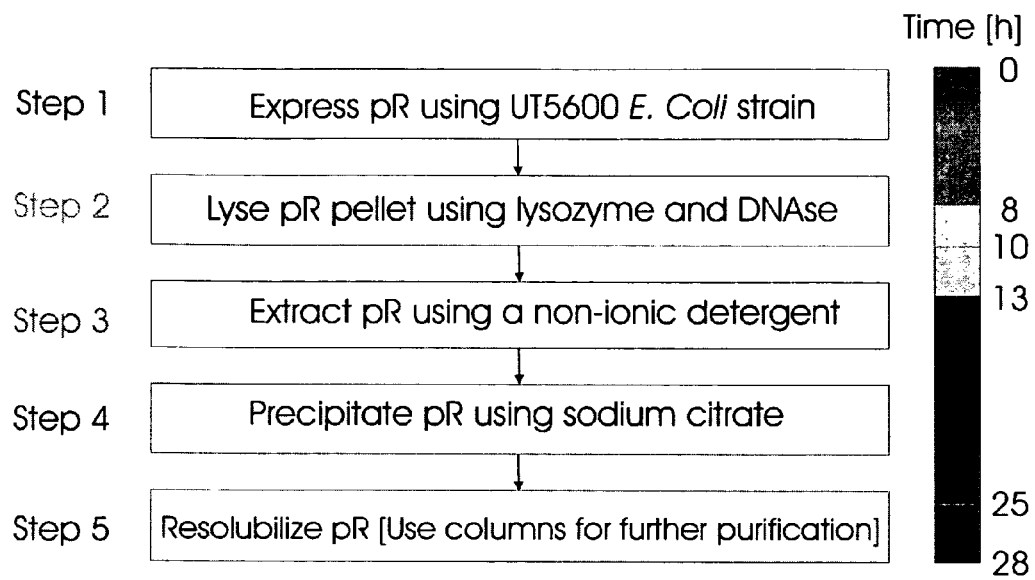
FIG. 3 is schematic representation of the citrate purification procedure of the present invention with a timeline.

The present invention includes a purification method, based on the use of citrate as a precipitant in the presence of a low concentration of non-ionic detergent such as β-octylglucoside or Triton-X100. We have optimized these conditions to allow us to precipitate pR selectively from among all the membrane proteins and lipids that are present in a detergent extract of *E. Coli* cells, giving a high yield of pR at ~30%-50% purity (dry weight) in a single step, by using inexpensive materials and apparatus. This simple and rapid method is suitable as a preliminary purification for poly-Hismodified pR and related site-directed mutants, to be followed by a nickel-resin column to yield high-purity protein. However, one advantage of the citrate purification procedure is that it also provides a means to obtain largely-pure pR without utilizing the poly-His-tag. That is, our purification method is not strongly dependent on any particular sequence element in pR, and can therefore be applied to the particular wild type sequence that we have investigated, as well as proteins with somewhat different primary sequences, such as site-directed mutants.

The present invention includes a method of purifying pR by using selective precipitation under carefully specified conditions of detergent concentration, pH, and the presence of an inexpensive pR-specific precipitating agent (specifically, citrate). Thus the need for chromatography is reduced or completely eliminated, depending on the purity level required for subsequent use of the pR. The pR obtained from a single citrate precipitation (followed by low-speed centrifugation) directly yields a quantity and purity of protein satisfactory to investigate and/or exploit many material properties of pR, including the band position(s) on SDS (sodium dodecylsulfate) polyacrylamide gel electrophoresis, the visible absorption spectrum, and the transient differential IR absorption spectrum.

The ability to purify pR without requiring any Ni-NTA resin greatly reduces the cost of materials required for purification (by several dollars per mg), as well as the amount of skilled technician time required to obtain the pR. Furthermore, the citrate purification method has proved to be directly applicable to pR-related proteins, i.e. proteins that are slightly different in sequence from that for which the method was originally developed. This will be of particular value in purifying mutant proteins that have properties tailored to particular applications. In particular, the citrate purification methods will be of enormous value if a need arises to express pR without any poly-His tag (e.g. from its natural source organisms when they are cultivated from the world's oceans). This simple purification method will likely help industrial-scale purification of pR become cheaper and more efficient, improving its potential for use as a material in non-linear optical films, holographic interferometers, and other optical and molecular-electronic devices.

The invention will be further illustrated with reference to the following specific example. It is understood that this example is given by way of illustration and is not meant to limit the disclosure or the claims to follow.

EXAMPLE

*Escherichia coli* (*E. coli*) cells (UT5600) expressing wild type pR were provided as a gift by Oded Béjà. The *E. coli* had been transformed with a plasmid containing the pR gene under the control of the Ara promoter, which can be controlled by arabinose in the growth medium. This expression plasmid was recovered from the provided strain using Wizard™ Plus Midipreps DNA Purification System (Promega Biotech).

The *E. coli* strain UT5600 was used for expressing the wild-type and mutant pR. *E. coli* was routinely grown in an enriched Luria-Bertani (LB) media containing (per 1L):

a. Tryptone: 10 g
b. Yeast extract: 5 g
c. 50 mM $NaH_2PO_4$
d. 50 mM $K_2HPO_4$
e. 0.75 mM $MgSO_4$
f. Glycerol.: 2% (w/v).

The pH was adjusted to 7.0 before autoclaving the media. When needed ampicillin (amp) (50 μg/mL) was added to the media.

The UT5600 cells were obtained by curing (removing the plasmid from) a sample provided by O. Béjà containing the plasmid pBAD-TOPO. This recovered strain was re-transformed with the mutant plasmids by using a standard $CaCl_2$ treatment procedure to make the cells competent.

Protein Expression:

Individual colonies of transformed cells were selected from LB-amp plates, and were then grown to late log phase. Protein expression was carried out using mostly small scale growth and occasionally using fermentors. The procedure used for both the methods were nearly identical with regard to growing time and induction. The methods follow the basic outlines as published by Krebs et al. (2002) with several modifications.

For the small scale protein expression, a late log phase culture was diluted 10-fold and allowed to incubate for an additional 2 h at 37° C. before being induced with 0.2% L-arabinose for 4 h at 37° C. For a maximum yield of pR, it was very critical to add the inducer just as the doubling time of the cells began to increase. The operations were performed in a 1-L flask containing 400 mL enriched LB media in shaker baths (180-220 rpm). Growth was monitored by measuring the optical density at 600 nm. Large scale fermentation involved using 10 L flasks with continuous paddle and aeration.

Cell Harvesting and Chromophore Regeneration:

After the 4-hr induction period, the cells were centrifuged at 5500 rpm in a fixed-angle rotor at 4° C. for 45 min in a Beckman GPR tabletop centrifuge. Then the supernatant was discarded and the pellet was re-suspended in 5 mM HEPES, pH 7.1. This suspension was centrifuged again at 5500 rpm at 4° C. for 45 min. The previous two steps were repeated again to obtain the *E. coli* cell pellet. This pellet was generally white or light grey in color.

This cell pellet was re-suspended in a minimal amount of 5 mM N-2-hydroxyethylpiperazine-N'-2-ethanesulfonic acid (HEPES) along with 50 μg all-trans retinal solution (in acetone). This was followed by stirring for 30-180 min at 4° C. using a magnetic stir-bar. The cells were then centrifuged at 5500 rpm at 4° C. for 45 min. The supernatant was discarded to obtain the bright red colored pellet containing pR.

In some of the experiments, the retinal chromophore was added along with L-arabinose during the induction period. This produced a red pellet immediately upon harvesting the cells. This modification saves time by cutting down an additional step.

Cell Lysis:

The regenerated pellet was re-suspended in minimal amount of 5 mM HEPES. To this suspension lysozyme (0.3 mg/mL) was added as a powder along with a small amount (several nM) of the protease inhibitor AEBSF and DeoxyRiboNuclease. The cells were then incubated for 60-180 min at 4° C., resulting in removal of the cell wall. This was followed by centrifugation at 7500 rpm at 4° C. for 30 min. The clear supernatant was discarded and the lysed red-colored pellet was used to extract pR.

Optimized Citrate-purifcation Procedure:

The following steps yielded pR in a rapid and inexpensive fashion.
   a. For 15 g (wet weight) of the lysed pR pellet, 40 mL of 10 mM HEPES, pH 7.1 and 3.0% β-octyl-D-glucoside (OG) as dry powder was added.
   b. The pellet was allowed to stir constantly in the detergent solution for 120-240 min at 4° C. in dark conditions.
   c. This was followed by centrifugation for 30 min at 5500 rpm at 4° C. The residue, consisting mainly of cell debris, was discarded (If there were any signs of reddish color in the cell debris, it was used for one more extraction as in step b).
   d. The supernatant was diluted using 100 mM sodium citrate solution, pH 6.0, to bring down the concentration of OG from 3.0% to 0.5%.
   e. This was followed by centrifugation for 5 min at 5500 rpm at 4° C. Any white precipitate was discarded.
   f. The supernatant was further diluted to an OG concentration of ~0.25% using 100 mM sodium citrate, pH 5.5. This solution was incubated at 4° C. for 8-12 h (until precipitation could be visually seen).
   g. After incubation the suspension was centrifuged at 5500 rpm for 30 min at 4° C. This time the clear supernatant was discarded.
   h. The bright-red pR pellet was re-solubilized in a minimal amount of 3.0% OG in 10 mM Tris-Cl pH 9.5 and allowed to stir for 30 min at 4° C.
   i. The re-solubilized pR was centrifuged at 5000 rpm for 5 min at 4° C. to sediment any unsolubilized material.
   j. The supernatant was subjected again to steps (d) to (i) to obtain substantially pure pR. However, this time the incubation time of 8-12 h is unnecessary as precipitation occurs instantly.

Search for and Optimization of Precipitant:

Samples of pR, typically at a concentration of 1 mg/mL in buffer A containing 3.0% OG and in a volume of 0.2 mL, were each treated with various volumes of several simple organic salts at pH values in their buffering range (sodium citrate, pH 3.0-6.0; sodium acetate, pH 4.0-6.0; HEPES, pH 6.5,7.0; glycylglycine, 7.5-9.0; glycine, 9.5-10.5; final concentration: 100 mM each). The samples were incubated 18 h at 4° C., and then centrifuged (5 min, 3000 g) to search for signs of precipitation of pR.

Polyacrylamide Gel Electrophoresis:

A 12% discontinuous SDS/polyacrylamide gel was used for molecular weight and purity analysis.

Absorption Spectroscopy:

The absorption spectra were recorded either on a Shimadzu UV-265 spectrophotometer or on a Cary 50 Bio UV-Visible spectrophotometer (Varian, Inc CA) with a resolution of 1-2 nm, at room temperature. Measurements were made using a masked quartz cuvette with a maximum volume of 1 mL. The data collected were analyzed using MIDAC-GRAMS® (Galactic Industries) software.

Determination of Optimum Conditions for Selective Proteorhodopsin Precipitation by Citrate:

Aliquots of a pR sample that had previously been purified using a Ni column (typically 1 mg/mL in 5 mM HEPES, pH 7.1 and solubilized in 3% OG) were each treated with a high concentration of one of a number of buffers at different pH values (citrate, pH 3.0-6.0; HEPES, pH 6.5-7.0; glycylglycine, 7.5-9.0; glycine, 9.5-10.5; final concentration: 100 mM each). Upon subsequent incubation overnight at 4° C., citrate treated samples in the pH range 4.0-6.0 were found to undergo precipitation, which was not seen for any other pH values ranging from 6.5 to 10.5. That is, a bright red pellet was obtained in the samples containing a citrate buffer, whereas no pellet was seen in the other samples (all of which were at higher pH). This provided the first clear evidence that pR has unusually low solubility in citrate buffer pH 4.0-6.0.

To examine whether the precipitating effect was only due to the choice of citrate as buffer or the pH itself, 1 part of pR solubilized in 3.0% OG was treated with 8 parts of sodium acetate buffer (100 mM, containing 0.3% OG) at several different pH values in the range 4.0-6.0. In these cases, no sign of precipitation was seen.

Screening Experiments:

It was subsequently discovered that adding citrate buffer (20-100 mM final concentration; pH 5.0-7.0) to purified pR in random volumes and at random OG concentrations did not always cause precipitation. Furthermore, even when precipitation did occur, it typically was not immediate but rather required overnight incubation. Thus it was important to screen the exact conditions for the precipitation of pR.

For initial screening, and with an eye towards using the citrate precipitation as a purification method, we decided to use impure pR in the form of a fresh 3.0% OG extract of cholate-washed E. coli membranes, instead of Ni-column-purified pR, for further experiments involving the citrate buffer.

The aim of these experiments was to determine sets of pH, citrate concentration, and detergent concentration conditions that allowed for selective precipitation of different sets of proteins in the impure pR sample. The ultimate goal was to be able to take an impure sample containing pR and precipitate the pR at some set of conditions, but not until after first having removed as many protein impurities as possible by precipitating them under sub-critical conditions.

Before the full screening experiments were performed, two important thresholds were determined. These concentration thresholds had to be reached in order for any precipitation of pR to occur (at least with the impure samples we were initially working with.) (a) The concentration of the OG detergent in the incubating sample needed to be below ~0.5%. (b) The concentration of citrate needed to be above ~30 mM.

The full screen to determine the conditions for precipitation took into account three major factors, namely the pH, concentration of the detergent, and the concentration of the citrate buffer. Looking at the color of the pellet provided an immediate visual means of identifying whether native protein could be obtained by the precipitation conditions. FIG. 3.9 shows the different conditions that were examined. (In every case, the sample was incubated for 8-12 h at 4° C. in the dark, and then centrifuged at 3000 g for 20 min) The most intense colored pellet was obtained at pH 5.5 when the OG concentration was 0.3% and the final citrate concentration was 50 mM.

The results from the screening experiments provide the basic conditions needed for the purification using citrate and non-ionic detergents. The detergent must be diluted (with the citrate buffer, pH ~5-6), initially from a concentration above the critical micellar concentration (CMC) to one close to the CMC value in order to precipitate impurities, and then to a final concentration somewhat lower in order to precipitate the pR. In general, we have settled on using citrate concentration of 100 mM, although it gives substantially the same result as with 50 mM.

Protein Purification Data:

Data for pR Extraction:

To examine the purity and nature of the protein after the precipitation procedure, UV-Visible Spectroscopy and SDS-PAGE (polyacrylamide gel electrophoresis) experiments were performed. Even after precipitation and re-solubilization, the protein remains stable with a bound retinal chromophore, evident from the 545 nm absorption maximum indicative of a properly folded protein with a bound chromophore.

Keeping in mind the commercial applicability of the citrate precipitation procedure towards purifying proteorhodopsin, a large scale purification was performed. The results of this purification method are shown in Table 1. The procedure looks very promising and still can be progressed in certain steps to make it even more efficient. An area of improvement is the inability to completely precipitate all the pR after the first step of incubation with citrate. About 50% of the protein remains in the supernatant and cannot be readily precipitated. Currently, additional enzymes are being tested to help precipitate the pR being held in the supernatant. There is a strong possibility that E. coli lipids are providing resistance and shielding the protein from citrate, disabling it from precipitation. Similar experiments performed on a smaller scale usually resulted in a higher purity level.

However, it is important to note the positive features of this procedure. It is very easy to obtain over 32% pure protein in a few easy and inexpensive steps. The need for an ultracentrifuge is totally eliminated, since there is no need to spin any detergent solubilized membranes. Almost all transmembrane protein purification procedures involve this high-speed centrifugation step.

Figure 5:
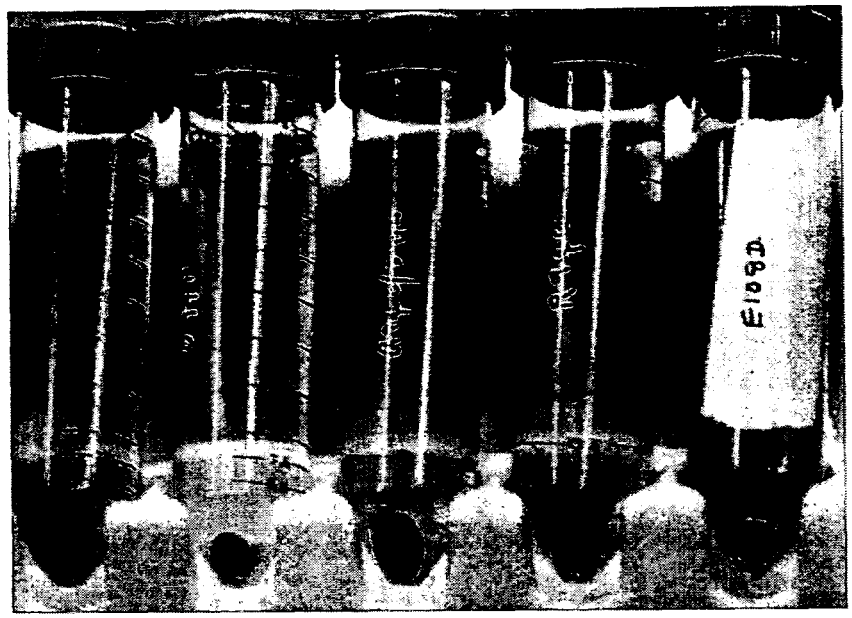
FIG. 5 is a picture of pellets of pR mutants obtained by citrate precipitation and (at far left) a dilute pR solution in octylglucoside prior to citrate addition.

Applicability of the Citrate Precipitation Procedure to Various pR Mutants:

One of the most important features of this purification method is its immediate applicability to closely-related variants of pR. Several mutants of pR with the polyhistidine tag were purified using this method (FIG. 5). The conditions for the precipitation of pR was similar to the one used for the wild-type pR. This result proved that the method was not specific to the sequence of the wild-type pR.

The pR triple cysteine mutant [C(107,156,175)S] (TCM), in which all the 3 native cysteines were replaced by serine (Krebs et al. 2002), has 3 sulfur atoms substituted by oxygens. However, TCM is thought to differ by more than these 3 atoms from the wild-type pR, since it is believed not to possess a post-translational modification that is seen in fresh wild-type pR samples (Krebs et al. 2002). Nevertheless, the TCM can be purified quite easily by using the citrate purification method.

In fact, some data demonstrate that the citrate purification method is even more powerful for the TCM than for the wild type. This is because a shorter incubation time in 100 mM citrate pH 5.5 (<30 min) is sufficient to obtain nearly-complete precipitation on freshly-prepared TCM in 0.3% octylglucoside, whereas overnight incubation is needed for the wild-type protein. That is, TCM (without the post-translational modification) clearly precipitates at a faster rate than the wild-type pR. This suggests that the as-yet unidentified post-translational modification could be inhibiting precipitation in the presence of citrate. We also observed that citrate-purified wild-type pR, upon resolubilization in 3% octylglucoside pH 7.1, followed by subsequent treatment with more citrate, immediately precipitates, i.e. it behaves more like the TCM than the freshly-prepared wild type pR.

To identify the specific mutation in the TCM pR, which causes it to precipitate rapidly than the wild-type pR, single mutants C107S, C156S and C175S were prepared as described in the Methods section. The most important observation was the rapid precipitation of C107S when citrate was added to dilute the 3.0% octylglucoside solubilized C107S to 0.2% octylglucoside. This was similar to the TCM pR. However, the other two cysteine mutants C156S and C175S did not precipitate immediately but required an incubation of 8-12 hrs similar to the wild-type pR. This leads to a speculation that the C107S mutant is specific to the rapid purification procedure for pR.

Advantages of the Precipitation Procedure:

This method demonstrates a highly selective condition wherein the protein of choice is precipitated without denaturation. The ability to purify a membrane protein up to 32% pure (Table 1) using simple salt precipitation and varying pH conditions has not yet been reported in the literature. To achieve the precipitation of the protein the main factors to be adjusted are the detergent concentration, pH and sodium citrate concentration. Each factor has its importance in the success of the procedure. The need for high speed centrifugation is completely eliminated in this procedure. By solubilizing the protein in a non-ionic detergent followed by precipitation, the need for spinning down detergent solubilized membranes is eliminated. This cuts the cost for large scale purification of proteorhodopsin.

It is also important to work with a native protein sequence without any C-terminal tags which could create problems with the structure and finction of the original protein. This means working with a protein without any histidine tags. Without histidine tags, the protein cannot be purified using nickel resin columns. However, the citrate purification procedure completely eliminates the need for any Ni resin columns to obtain protein with reasonable purity (~35%). Further purification can be done using hydroxyapatite columns which are relatively cheap when compared to Ni resins. This is highly advantageous from a commercial viewpoint considering the fact that proteorhodopsin has a great potential for usage in optical information processing.

The other interesting feature is the ability of sodium citrate to act as a precipitant. The conditions to precipitate pR selectively can be used in crystallization experiments to obtain well-defined pR crystals to elucidate the three dimensional structure. There is a possibility that this procedure could be used to purify other transmembrane proteins, especially GPCR's which have high pharmaceutical significance. This procedure is a novel method to easily, efficiently and inexpensively purify a membrane protein and has never before been described in the literature.

Another class of membrane proteins for which the present purification procedure is likely useful is the G-protein-coupled receptors (GPCRs). Like pR. and bR, G-protein GPCR's are 7-helix integral membrane proteins, which activate G-proteins when bound to specific ligands. They form the largest family of cell-surface receptors mediating responses to various signal molecules, hormones, and neurotransmitters. Approximately 1700 GPCR genes may be present in the human genome (Haga and Berstein, 1999), but of these only a few have even been isolated from cells as proteins. GPCR's have been identified as the targets for drugs currently making up nearly half the pharmaceutical market in the US. It is therefore important to understand the mechanism behind their action.

As of 2003, bovine rhodopsin (the light-activated photoreceptor in the eye), is the only GPCR whose crystal structure has been elucidated (Palczewski ci aL, 2000). The reasons why a new membrane protein purification method would have great utility in the field of GPCR structure determination are clear. Knowledge of a pharmaceutical drug's target protein structure is the key to designing improved drugs. Knowledge of the structure of a GPCR for which no known drug has activity is a key to defining the role of the protein as well as to identifying endogenous and exogenous ligands that have a role in modulating cellular activities.

As has been noted by others (Haga and Berstein, 1999), "The first difficulty in structural determination is that except rhodopsin, sufficient amounts of GPCR's cannot be readily attained. Large-scale expression and purification of GPCR's is therefore a prerequisite for structural studies." In general, several milligrams of pure, homogeneous and functionally active protein are a requirement for various in vitro studies on the structural and functional aspects of the protein. Therefore any technique that provides an easier route in large-scale purification of membrane proteins (GPCRs in particular) will quickly become an invaluable technique in the pharmaceutical industry.

The structural similarity between GPCRs and pR is the basis for applying our inexpensive method specifically to the purification of GPCRs. The GPCRs have a similar transmembrane topology as pR, with the N-terminus located intracellularly, the C-terminus extracellular, and 7 transmembrane α-helices in between. The organization of amino acid side chains along the α-helices generally follows similar patterns, with predominantly lipophilic residues interrupted periodically (at a periodicity of roughly 3-4 residues) by hydrophilic or charged side chains. The organization of charged groups on the loops connecting the helices at the membrane surfaces is also somewhat similar, with a net negative charge on the extracellular surface and a more positive net charge on the intracellular surface. The exact detergent and citrate concentrations needed to selectively precipitate each particular GPCR are expected to be dependent on its exact properties, such as its isoelectric point and its exposed hydrophilic surface. However, the methods described herein provide a clear demonstration of how it is possible to determine empirically through simple tests the optimal conditions for each particular GPCR.

We have demonstrated a novel purification method, the first of its kind in membrane proteins, in which simple salt and pH conditions are utilized to selectively precipitate the protein of interest in a native state from a non-ionic detergent solution. This method has been optimized for a medium-scale (10-100 mg scale) production of pR, a candidate with great potential for usage in the field of information processing in the years to come. An important feature of the purification method is the low cost required to obtain a substantially pure protein likely to be of direct use in optical information-storage or molecular-electronic devices. The existing art of pR purification has involved a final step requiring expensive materials and/or a time-consuming column purification that requires the use a substantial amount of a trained operator's time, and/or the use of expensive capital equipment (robots) to complete. With the present purification, the column procedure(s) can be replaced by a single easy rapid step involving cheaper materials.

The method also demonstrates the effect of the post-translational modification in the wild-type pR involving the native cysteines. This modification could play a crucial role in the experiments needed to determine the 3-dimensional structure of pR using X-ray crystallography. Future experiments involving similar conditions could be used to purify other membrane proteins, which are currently purified using expensive and difficult methods.

While the invention has been described with preferred embodiments, it is to be understood that variations are to be considered within the purview and the scope of the claims appended hereto.

TABLE 1

| | |
|---|---|
| Amount of LB media used | 4800 ml |
| Wet weight of wt-pR ($His_6$+) pellet | 57.8 g |
| Wet weight after lysis | 55.65 g |
| Discarded wet weight of pellet (after extraction with 3.0% octyglucoside | 41.3 g |

| Step | Amount mg | Purity % | Yield % |
|---|---|---|---|
| After extraction with 3.0% Octyglucoside | 56 | 16.8 | 100 |
| After first precipitation with sodium citrate | 29.07 | 28.6 | 51.9 |
| After second precipitation with sodium citrate | 26.74 | 31.8 | 47.75 |
| After Nickel resin column purification | 22.70 | 39.9 | 40.53 |

Protein purification data obtained from a large scale purification process of wild-type pR using sodium citrate as the precipitant, followed by column purification using Ni resin. The amount of protein was calculated using absorption spectroscopy as described in Krebs et al. (2002). The spectra corresponding to different stages of purification in the table is shown in FIG. 1.

What is claimed is:

1. A method for purifying a 7-helix membrane protein comprising:
   providing a non-ionic detergent solubilized test sample comprising a target 7-helix membrane protein;
   adding incremental amounts of a citric acid or a salt thereof to the test sample to form one or more mixtures; and
   treating the one or more mixtures under conditions effective to avoid denaturation and to obtain an aggregated target 7-helix membrane protein, wherein the one or more mixtures are maintained at a pH of between about 4.5 and about 6.5, a detergent concentration of up to about 0.5%, and a citric acid concentration of about 30-100 mM.

2. The method according to claim 1, wherein the non-ionic detergent is β-octylglucoside.

3. The method according to claim 1, wherein the non-ionic detergent is maintained at a concentration of about 0.25 to about 0.35%.

4. The method according to claim 1, wherein the citric acid or salt thereof is added as a solution having a pH of from about 3 to about 6.

5. The method according to claim 1, wherein the membrane protein is wild-type proteorhodopsin having a C-terminal polyhistidine tag.

6. The method according to claim 1, wherein the membrane protein is wild-type proteorhodopsin having all three cysteine residues mutated to serines.

7. The method according to claim 1, wherein the membrane protein is a G-protein-coupled receptor.

8. The method according to claim 1, wherein said adding comprises:
adding one or more amounts of the citric acid or a salt thereof to precipitate out impurities in the test sample, and
adding one or more amounts of the citric acid or a salt thereof to precipitate out the target 7-helix membrane protein.

9. The method according to claim 1, wherein said treating comprises subjecting the one or more mixtures to centrifugation.

10. The method according to claim 1 further comprising:
subjecting the aggregated target 7-helix membrane protein to chromatography.

11. A method for purifying proteorhodopsin comprising:
providing a non-ionic detergent solubilized test sample comprising proteorhodopsin;
adding incremental amounts of citric acid or a salt thereof to the test sample to form one or more mixtures; and
treating the one or more mixtures under conditions effective to avoid enaturation and to obtain an aggregated proteorhodopsin protein, wherein the one or more mixtures are maintained at a pH of between about 4.5 and about 6.5, a detergent concentration of up to about 0.5%, and a citric acid concentration of about 30-100 mM.

12. The method according to claim 11, wherein the non-ionic detergent is β-octylglucoside.

13. The method according to claim 11, wherein the non-ionic detergent is maintained at a concentration of about 0.25 to about 0.35%.

14. The method according to claim 11, wherein the citric acid or salt thereof is added as a solution having a pH of from about 3 to about 6.

15. The method according to claim 11, wherein the proteorhodopsin is wild-type proteorhodopsin having a C-terminal polyhistidine tag.

16. The method according to claim 11, wherein the proteorhodopsin is wild-type proteorhodopsin having all three cysteine residues mutated to serines.

17. The method according to claim 11, wherein said adding comprises:
adding one or more amounts of the citric acid or salt thereof to precipitate out impurities in the test sample, and
adding one or more amounts of the citric acid or salt thereof to precipitate out the proteorhodopsin.

18. The method according to claim 11, wherein said treating comprises subjecting the one or more mixtures to centrifugation.

19. The method according to claim 11 further comprising:
subjecting the aggregated proteorhodopsin to chromatography.

20. The method according to claim 1, wherein the one or more mixtures are maintained at a pH between 4 and 6.

21. The method according to claim 11, wherein the one or more mixtures are maintained at a pH between 4 and 6.

* * * * *